(12) United States Patent
Haim et al.

(10) Patent No.: US 6,198,963 B1
(45) Date of Patent: Mar. 6, 2001

(54) POSITION CONFIRMATION WITH LEARN AND TEST FUNCTIONS

(75) Inventors: Shlomo Ben Haim, Haifa; Maier Fenster, Petach Tichva; Assaf Govari, Kiryat Haim, all of (IL)

(73) Assignee: Biosense, Inc., New Brunswick, NJ (US)

(*) Notice: Subject to any disclaimer, the term of this patent is extended or adjusted under 35 U.S.C. 154(b) by 0 days.

(21) Appl. No.: 09/079,338

(22) Filed: May 14, 1998

(30) Foreign Application Priority Data

Jul. 17, 1996 (IL) ........................................... 119262

(51) Int. Cl.[7] ........................................... A61B 5/05
(52) U.S. Cl. ..................... 600/424; 600/429; 600/431; 600/435; 128/899; 607/122; 607/156
(58) Field of Search ....................... 600/407, 409, 600/410, 411, 417, 418, 419, 422, 423, 424, 431, 429, 435, 437, 439, 440, 450, 451, 452, 455, 459, 462, 463, 466, 467, 481, 483, 484, 508, 529, 535; 128/653, 662, 660, 642, 644, 899; 607/115, 112

(56) References Cited

U.S. PATENT DOCUMENTS

| | | | |
|---|---|---|---|
| 4,905,698 | 3/1990 | Strohl, Jr. et al. | 128/653 R |
| 5,002,137 | 3/1991 | Dickinson et al. | 175/19 |
| 5,099,548 | 3/1992 | Besz et al. | 128/653.1 |
| 5,325,873 | 7/1994 | Hirschi et al. | 128/899 |
| 5,375,596 | 12/1994 | Twiss et al. | 128/653.1 |
| 5,391,199 | 2/1995 | Ben-Haim | 607/122 |
| 5,425,367 | 6/1995 | Shapiro et al. | 128/653.1 |
| 5,425,382 | 6/1995 | Golden et al. | 128/899 |
| 5,443,489 | 8/1995 | Ben-Haim | 607/115 |
| 5,558,091 | 9/1996 | Acker et al. | 128/653.1 |
| 5,622,169 | 4/1997 | Golden et al. | 128/653.1 |
| 5,645,065 | * 7/1997 | Shapiro et al. | 128/653.1 |
| 5,715,822 | 2/1998 | Watkins et al. | 128/653.5 |
| 6,004,269 | * 12/1999 | Crowley et al. | 600/439 |

FOREIGN PATENT DOCUMENTS

| | | |
|---|---|---|
| WO 94/04938 | 3/1994 | (WO). |
| WO 96/05768 | 2/1996 | (WO). |
| WO 9632060 | 10/1996 | (WO). |
| WO 97/03609 | 6/1997 | (WO). |

* cited by examiner

Primary Examiner—Marvin M. Lateef
Assistant Examiner—J. Lin
(74) Attorney, Agent, or Firm—Louis J. Capezzuto

(57) ABSTRACT

Verification apparatus (32), for verifying the location of an object (22) in a patient's body (20), the apparatus having learn and test modes and including a receiver (76), which receives signals from the object responsive to the location thereof. A parameter vector is derived from the signals. A memory (58) records a learn value of the parameter vector in the learn mode. A processor (54) receives a test value of the parameter vector in the test mode, and determines whether the test value is within a predetermined range of the learn values so as to verify the location of the object (22).

38 Claims, 14 Drawing Sheets

POSITION CONFIRMATION WITH LEARN AND TEST FUNCTIONS

FIELD OF THE INVENTION

The present invention relates generally to the field of intrabody tubes, i.e., tubes used internally in the medical care of patients, and specifically to location confirmation of medical tubes within a human body.

BACKGROUND OF THE INVENTION

In many instances medical tubes are inserted into a patient's body for short-term or long-term infusion of medicine, blood products, nutrition or other fluids. Such tubes are inserted, for example, into the patient's venous, arterial or digestive system. Sometimes it is important to insert the medicine or other fluid into a particular point in the patient's body. For example, in cancer chemotherapy and antibiotic therapy, an outlet of the tube infusing the medicine must be positioned in an area of high volume blood flow. As another example, patients who cannot eat on their own have a feeding tube inserted through their nose or mouth into their stomach. A feeding solution is inserted into the patient's stomach through an end of the feeding tube outside of the patient's body. The feeding solution naturally must be inserted into the stomach and not into other areas of the body. Other intrabody tubes include dilating tubes to widen esophageal stricture, colonic decompression tubes and urological tubes.

In many cases, an intrabody tube is used periodically over a long period of time. Therefore, to avoid the need to repeatedly insert new tubes, the tube is left within the patient's body. This is especially important when the patient is in home care, where there is nobody who can insert the tube. Home care of patients is a widespread and growing field, mainly due to the rising cost of hospital fees and the lengthening of care periods.

Generally, there is no simple method of keeping an intrabody tube fixed in place, and the tubes do not always remain in their original place. The outlet of the tube may drift out of place within the patient's body. Using the tube when its outlet is not in its proper place may cause serious damage. For example, the tip of a feeding tube may curl up and drift to the patient's lungs. Inserting a feeding solution through the tube in such a case could cause the death of the patient. Likewise, a chemotherapy infusion tube must be placed in a suitable location with a large stream of blood, such as the superior vena-cava in the heart. Otherwise, the medicine may damage the lining of the vascular system. It has been found that of patients who receive medicine in their hearts through infusion tubes, a significant portion suffer from complications due to unnoticed drift of the infusion tube.

There are other cases in which it is desired to follow up on the location of objects, other than tubes, within a patient's body. For example, it may be desired to follow up on the location of a screw, staple, electrode, shunt or any other object implanted in a patient's body. A specific example involves a Murphy button, which is used to connect a torn part of the intestine. The Murphy button is implanted in the intestine, and should remain in place until the intestine heals. After the intestine heals, the Murphy button should drift along the intestine out of the patient's body. Medical staff usually follow up on the movements of the button in case it gets stuck within the patient.

Various methods of confirming the location of medical tubes have been shown in the art. X-ray imaging is the most commonly used location confirmation system. Position determining systems can also be used for this purpose.

U.S. Pat. No. 5,425,382, whose disclosure is incorporated herein by reference, describes apparatus and method for locating a medical tube. The tube is located using a detection apparatus which senses the static magnetic field strength gradient of a magnet associated with the tube. The user locates the tube according to the gradient magnitude at points along the patient's body.

Another method is disclosed in U.S. Pat. Nos. 5,099,845 and 5,325,873, whose disclosures are incorporated herein by reference, wherein a radiating resonant element is associated with the tube. Apparatus is provided to indicate the distance from the apparatus to the tube, according to the radiation levels at different points, whereby the position of the tube is determined.

Another type of position-sensing apparatus is described in U.S. Pat. Nos. 4,905,698 and 5,425,367, whose disclosures are incorporated herein by reference. Such apparatus generates AC currents which induce an electromagnetic field, which in turn induces currents within a coil at the tip of a catheter. According to these currents, the relative location of the catheter is determined.

The use of the above described apparatus is time consuming and therefore complicates the use of intrabody tubes. Also, to operate such apparatus, a certain level of skill and experience is required. Therefore, such apparatus needs to be operated by clinical staff, and is not fit for widespread home care use.

SUMMARY OF THE INVENTION

It is an object of some aspects of the present invention to provide simple verification devices and methods for confirmation of intrabody tube location, which can be operated by nonprofessionals.

It is an object of some aspects of the present invention to provide simple verification devices and methods for quick confirmation of intrabody tube location.

It is an object of some aspects of the present invention to provide a verification device for automatic confirmation of intrabody tube location.

It is a further object of some aspects of the present invention to provide verification devices for confirmation of intrabody tube location which prevent use of the tube unless it has been confirmed that the tube is properly located.

Another object of some aspects of the present invention is to allow simple follow-up of the movements of an object within a human body.

Israel patent application number 119262, filed on Sep. 17, 1996, and PCT patent application PCT/IL97/00058, filed Feb. 14, 1997, which are assigned to the assignee of the present invention and whose disclosures are incorporated herein by reference, disclose methods of determining whether a chemotherapy tube has remained in its original position.

In some preferred embodiments of the present invention, a verification device outside the body of a patient is used to confirm the location of a medical tube's outlet inside the body. Preferably, the verification device operates in two modes, a learn mode, which records the correct location of the tube's outlet, and a test mode, which confirms, at later times, that the outlet remains in the correct location. Preferably, in the learn mode, the verification device measures and records one or more parameter values, forming a parameter vector, which characterize the location of the tube's outlet relative to the verification device. In the test mode, the device confirms that the values of the parameter vector did not change significantly relative to the recorded values, i.e., the tested values are within an allowed range of the recorded values.

The allowed range is necessary in order to minimize false alarms due to inaccuracy in the measurement or slight movements of the outlet of the tube which are insignificant. Preferably, the allowed range is defined such that proper location of the outlet is not confirmed when the outlet is in a dangerous position. The allowed range corresponds generally to areas in the patient's body where the tube may safely be used and/or areas regarding which there is substantially no risk that harm could be caused to the patient.

In some preferred embodiments of the present invention, a sensor is fixed to the medical tube, preferably, near the tube's outlet. The sensor enables the verification device to determine the one or more parameter values.

In preferred embodiments of the present invention, the method of using the verification device includes two steps: the "learn" step of recording location information, and the "test" step of location confirmation before every use of the tube. These steps will now be explained in detail.

The "learn" step is preferably performed by a professional clinical staff member. After the tube is inserted into the patient's body, the staff member preferably confirms that the tube's outlet is properly located. The confirmation is performed using any confirmation method known in the art, such as X-ray imaging, preferably without using the verification device. Alternatively, the verification device has a third mode, which allows professionals to determine the location of the sensor.

After the location of the outlet is confirmed, the verification device is brought to an anchor point adjacent to the body, from which the location is to be registered and, at later times, verified. Once the verification device has been brought to the anchor point, it is operated in the learn mode, to register location information for later confirmation. The learn mode preferably initiates measurement of the value of the parameter vector. Thus, the values of the one or more parameters are stored so as to be available for further use by the verification device in the test mode.

Preferably, the anchor point is on the patient's body, and is marked for further use, either by the clinical staff member or automatically by the verification device. The anchor point is preferably chosen such that the relative distance from the anchor point to the outlet of the tube is small and constant and does not change substantially when the patient changes his body orientation, or due to his breathing.

Alternatively, the changes in the relative distance due to the patient's breathing are avoided, by gating the verification device to operate only at a certain portion of the respiratory cycle. In addition, or alternatively, the changes due to the patient's breathing and body orientation may be taken into account when defining the allowed range of the one or more parameters, by defining a larger range.

In a further embodiment of the present invention, the verification device makes multiple measurements of the parameter vector during a period of time and determines and stores the entire range of the measured values of the parameter vector. Thus, changes in the one or more parameters due to the patient's breathing are taken into account, without impeding the accuracy of the location confirmation.

The test step is preferably simple, so that no prior knowledge or experience is needed by the user. Each time the tube is to be used, the verification device is brought to the anchor point and is operated in test mode. The verification device in the test mode measures and compares the value of the parameter vector with the stored value and, based on the comparison, reports whether the tube's outlet is correctly located or not. If the tube is not properly located, medical assistance must be obtained, and the tube must not be used.

In some preferred embodiments of the present invention, it may be necessary to confirm the location of more than one object within the patient's body. Similarly, to confirm the proper placement and orientation of a long tube, the location of more than one point along the tube may be confirmed. In such cases, more than one anchor point may be used, and users activate the verification device in both learn and test modes at all the anchor points successively, before the verification device produces a response. In this embodiment, the parameter vector has different members measured in each of the anchor points.

In some preferred embodiments of the present invention, the verification device is used to gate the flow of a fluid through the tube. The verification device prevents flow of liquid through the tube unless the verification device was operated in the test mode prior to the insertion of the liquid. Preferably, a signal indicating that the tube is in the proper position is passed from the verification device to a separate gate box. Alternatively, the tube runs through the verification device, which gates the flow. Thus, the verification device can be used in automatic infuision procedures.

In preferred embodiments of the present invention, measurement of the parameter vector is based on one or more signals transmitted to and/or from the sensor, which is fixed to the tube. Such signals could be ultrasound waves, ultraviolet waves, radio frequency (RF) waves, static or rotating electromagnetic fields, laser beams, etc. Preferably, the parameters used have a functional relationship with the distance between the verification device and the sensor. Alternatively or additionally, the parameters used have a functional relationship with the direction from the verification device to the sensor.

In some preferred embodiments of the present invention, the amplitude of an RF wave is measured. The verification device includes a measurement unit, which transmits an RF wave towards the sensor, which comprises a passive RF transponder. The sensor reradiates the wave back to the measurement unit which senses the amplitude of the reradiated wave. Alternatively or additionally, the signal's phase, variance, noise level, propagation time or any other parameter of the signal which has a functional relationship with the location of the sensor may be measured.

In one such preferred embodiment, the verification device makes measurements based on magnetic field coupling. The transponder preferably comprises three miniature coils connected in series or in parallel, which preferably have mutually linearly independent axes, and are most preferably orthogonally aligned with respect to each other. The verification device preferably includes a radiation coil, which generates a magnetic field that induces currents within the miniature coils of the sensor. The return effect of the currents induced in the miniature coils on the verification device is measured, and the distance from the miniature coils to the device is determined accordingly.

It is noted that although the present invention is described in relation to surgical tubes, it may be used to confirm the location of any object situated within a body, such as screws, staples, electrodes, shunts, buttons etc.

There is therefore provided in accordance with a preferred embodiment of the present invention a method of confirming a location of an object inserted into a human body, including:

measuring, by receiving signals from the object at a first time, a first value of a parameter vector which is dependent on the location of the object; and measuring a second value of the vector by receiving signals from the object at a later time, and determining whether the second value is within a predetermined range of the first value.

Preferably, the method includes controlling use of the object responsive to the second value.

Further preferably, controlling use of the object includes allowing use of the object only for a period of predetermined length after measuring the second value and determining that the second value is within the predetermined range.

Preferably, controlling use of the object includes controlling flow of a fluid through a medical tube.

Preferably, the method includes notifying a user at the later time whether the second value is within the predetermined range.

Preferably, notifying a user includes providing a warning to the user when the second value is outside the range.

Preferably, the method includes verifying the location of the object before measuring the first value.

Preferably, the body has a respiratory cycle, and measuring at the first and later times includes measuring at both times at substantially the same point in the respiratory cycle.

Preferably, measuring the values of the vector includes measuring a parameter vector which is dependent on the location of a medical tube inside the body.

Preferably, the method includes controlling flow through the medical tube responsive to the second value.

Alternatively or additionally, measuring at the first and later times includes receiving signals at a common checking location adjacent to the body.

Preferably, measuring at the first time includes marking the checking location on the body.

Preferably, receiving at the common location includes receiving signals at a plurality of checking locations in a predetermined order.

Preferably, measuring at the first time includes marking the plurality of checking locations according to the predetermined order.

Preferably, the parameter vector includes at least one member which has a functional relationship with a distance from its respective checking location to the object.

Preferably, measuring the second value includes receiving signals at one or more locations to find a location at which the second value is within the predetermined range.

Preferably, measuring the vector by receiving signals includes measuring a range of values of the signals during a period of measurement.

Alternatively or additionally, measuring the vector by receiving signals includes determining low bounds and high bounds of the range of values of the signals.

Alternatively or additionally, measuring the vector by receiving signals includes sensing a propagation time of the signals.

Alternatively or additionally, measuring the vector by receiving signals includes sensing an amplitude of the signals.

Alternatively or additionally, measuring the vector by receiving signals includes sensing a phase of the signals.

Alternatively or additionally, measuring the vector by receiving signals includes sensing a variance of the signals.

Alternatively or additionally, measuring the vector by receiving signals includes sensing a noise level of the signals.

Preferably, receiving signals includes receiving radio frequency waves.

Alternatively or additionally, receiving signals includes receiving acoustic waves.

Alternatively or additionally, receiving signals includes sensing a magnetic field.

Preferably, sensing the magnetic field includes sensing a gradient of the magnetic field.

Alternatively or additionally, receiving signals includes sensing an alternating magnetic field.

Preferably, sensing the magnetic field includes sensing a field of a magnet coupled to the object.

Preferably, sensing a field of a magnet includes sensing a field originating from a rotating magnet.

Alternatively or additionally, measuring the first and second values includes sensing currents induced within a coil.

Preferably, sensing the currents includes sensing currents induced due to a field originating from a coil mounted on the object.

Preferably, sensing the currents includes sensing currents induced within a coil mounted on the object.

Alternatively or additionally, measuring the first and second values includes charging and discharging a capacitor responsive to the currents in the coil.

There is further provided in accordance with a preferred embodiment of the present invention, a verification apparatus, for verifying the location of an object in a patient's body, said apparatus having learn and test modes and including:

a receiver, which receives signals from the object responsive to the location thereof;

signal analysis circuitry, which derives a parameter vector from the signals;

a memory, which records a learn value of the parameter vector received from the signal analysis circuitry in the learn mode; and a processor, which receives a test value of the parameter vector from the signal analysis circuitry in the test mode and determines whether the test value is within a predetermined range of the learn values so as to verify the location of the object.

Preferably, the apparatus includes an output, which provides a confirmation signal, dependent on whether or not the test value is within the predetermined range.

Preferably, the apparatus includes a gate, which receives the confirmation signal from the processor in the test mode and enables use of the object responsive thereto.

Preferably, the apparatus includes a user interface, which notifies a user of the apparatus in the test mode whether the test values are within the predetermined range.

Preferably, the processor provides a user with the values of the parameter vector, for verifying that the object is properly positioned before recording the one or more learn values.

Preferably, the parameter vector includes a parameter which is dependent on the distance from the apparatus to the object.

Preferably, the parameter vector includes a parameter which is dependent on the position of the object relative to the apparatus.

Preferably, the predetermined range includes a range indicative of the usability of the object.

Preferably, the apparatus includes at least one electromagnetic field transmitter, for inducing currents within a sensor mounted on the object, from which the receiver receives the signals.

Preferably, the receiver includes at least one coil, and the signal analysis circuitry measures currents induced within the coil by the sensor.

Preferably, the at least one receiver coil also serves as the electromagnetic field transmitter.

Preferably, the at least one receiver coil includes a plurality of coils.

Preferably, the plurality of coils includes a plurality of receiver elements, mutually spaced, each element including a plurality of mutually orthogonal coils.

Preferably, the signal analysis circuitry determines a low bound and a high bound of the parameter vector.

Preferably, the signal analysis circuitry measures a propagation time of the signals.

Alternatively or additionally, the signal analysis circuitry senses an amplitude, a phase, a variance or a noise level of the signals.

Preferably, the receiver includes a radio frequency wave receiver.

Alternatively or additionally, the receiver includes an acoustic wave receiver.

Alternatively or additionally, the receiver includes a magnetic field sensor.

Preferably, the magnetic field sensor includes a magnetic field gradient sensor.

Preferably, a first magnet is coupled to the object, and the apparatus includes a second magnet, which initiates a rotation of the first magnet, whose magnetic field is measured by the magnetic field sensor.

Preferably, the apparatus includes a user-actuated control, whereby the user initiates operation of the apparatus.

Preferably, the apparatus is actuated responsive to a polling signal.

Preferably, the apparatus includes a respiratory belt which determines a respiratory cycle of the patient, and the learn and test modes operate at substantially the same stage of the respiratory cycle.

Preferably, the object includes a medical tube, which is inserted into the patient's body, and a position sensor attached to the tube generates the signals that are received by the receiver.

Alternatively or additionally, the apparatus includes a gating valve, which allows flow through the tube when the processor determines that the test values are within the predetermined range of the learn values.

Alternatively or additionally, the apparatus includes an infuision pump which initiates verification of the location of the object periodically during the operation of the pump.

Preferably, the infusion pump initiates the operation of the verification device every time a fluid is to be inserted through the tube.

Preferably, the apparatus periodically verifies that the test values are within the predetermined range of the learn values, and including an infusion pump which is controlled to operate as long as the test values are within the predetermined range.

There is further provided in accordance with a preferred embodiment of the present invention, apparatus for controllably inserting a fluid into a patient's body, including:
 a controlled infusion device, which includes:
  a medical tube, for insertion into the patient's body; and
  a position sensor attached to the tube, which generates signals indicative of the position of the tube in the body; and
 a gating valve which allows flow through the tube responsive to verification of the position of the sensor, based on the signals.

Preferably, the position sensor includes a passive transponder.

Preferably, the position sensor has no wired connection to apparatus outside of the patient's body.

Preferably, the position sensor includes at least one coil, most preferably a single coil.

Alternatively or additionally, the position sensor includes a capacitor coupled to be charged through the coil.

Preferably, the position sensor includes a clamping circuit, through which the capacitor is discharged.

Alternatively, the position sensor includes at least three coils having mutually linearly independent axes.

Preferably, the at least three coils are connected in series.

Alternatively, the at least three coils are connected in parallel.

Preferably, the position sensor includes a magnet.

Preferably, the position sensor includes a rotating magnet.

Alternatively or additionally, the position sensor includes an acoustic transponder.

Preferably, the tube has an outlet in the patient's body and the position sensor is adjacent the outlet of the tube.

Preferably, the tube includes an intravenous tube.

Alternatively or additionally, the tube includes a gastric tube.

The present invention will be more fully understood from the following detailed description of the preferred embodiments thereof, taken together with the drawings, in which:

DETAILED DESCRIPTION OF PREFERRED EMBODIMENTS

Figure 1:
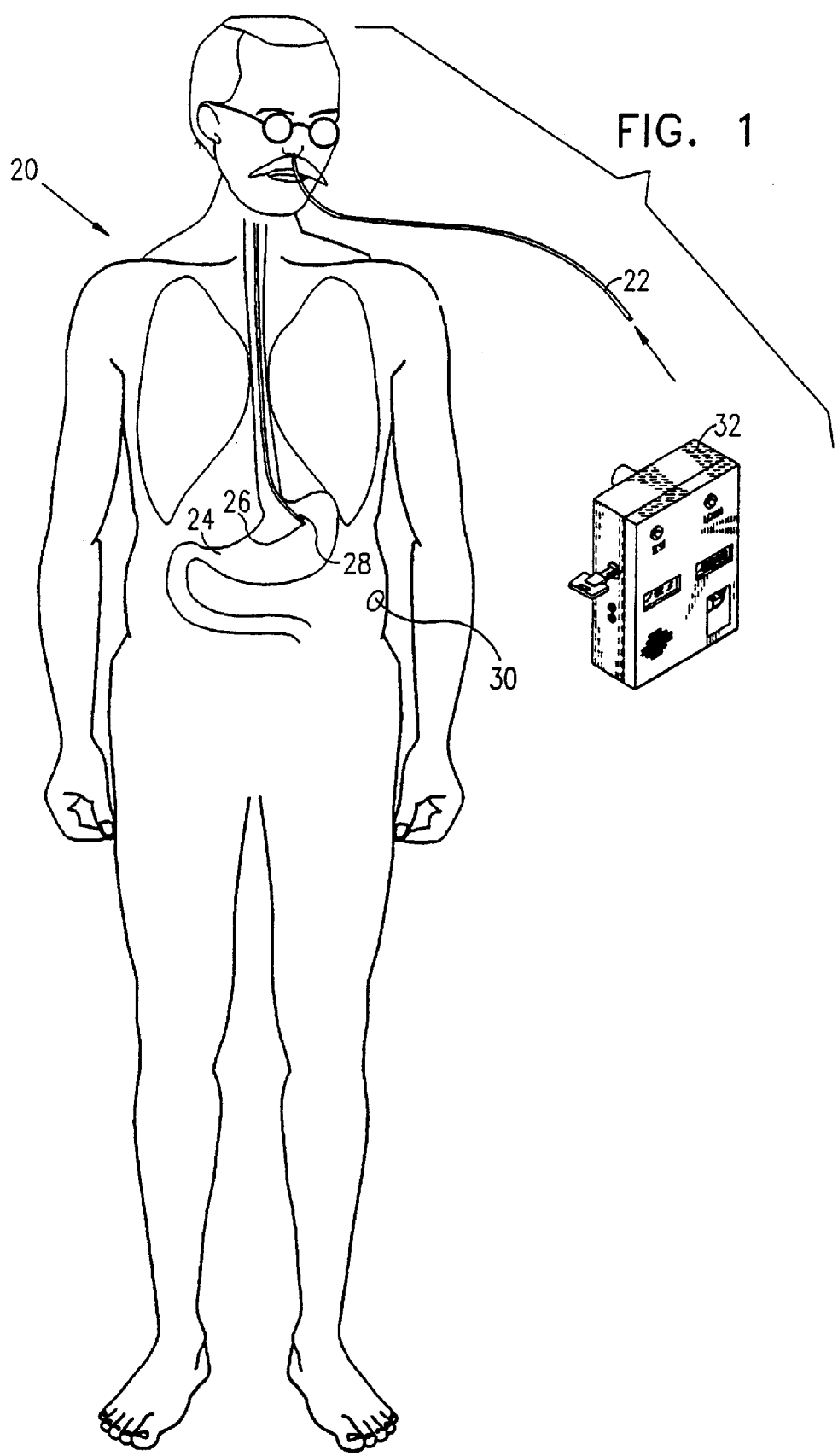
FIG. 1 is a perspective view of a patient with a feeding tube and a verification device, in accordance with a preferred embodiment of the present invention.

FIG. 1 shows a patient 20 with a feeding tube 22 running through his nose into his stomach 24, illustrating a preferred embodiment of the present invention. Tube 22 has an outlet 26 which is situated within stomach 24. A sensor 28 is fixed to tube 22, near outlet 26. An anchor point 30 is chosen and, preferably, marked on the patient's skin. A verification device 32 is placed against the skin at point 30. Preferably, point 30 is chosen so that its distance from stomach 24 is substantially constant, regardless of the patient's rest position. Sensor 28 operates in conjunction with verification device 32, as described below, to verify the position of outlet 26.

Figure 2A:
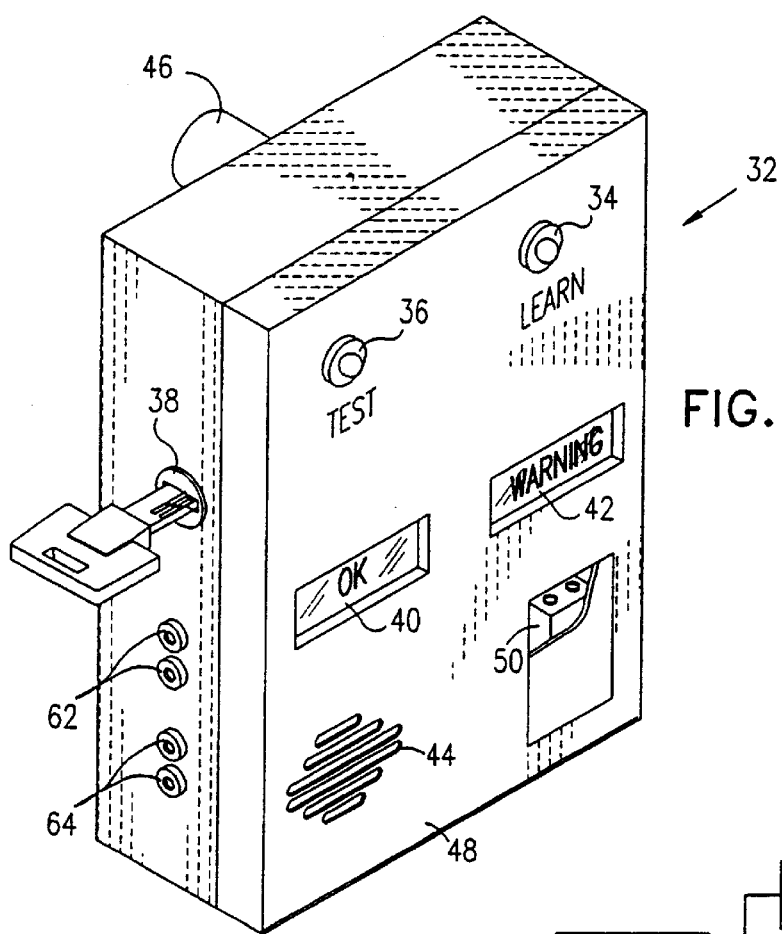
FIG. 2A is a perspective view of a verification device, in accordance with a preferred embodiment of the present invention.
Figure 2B:
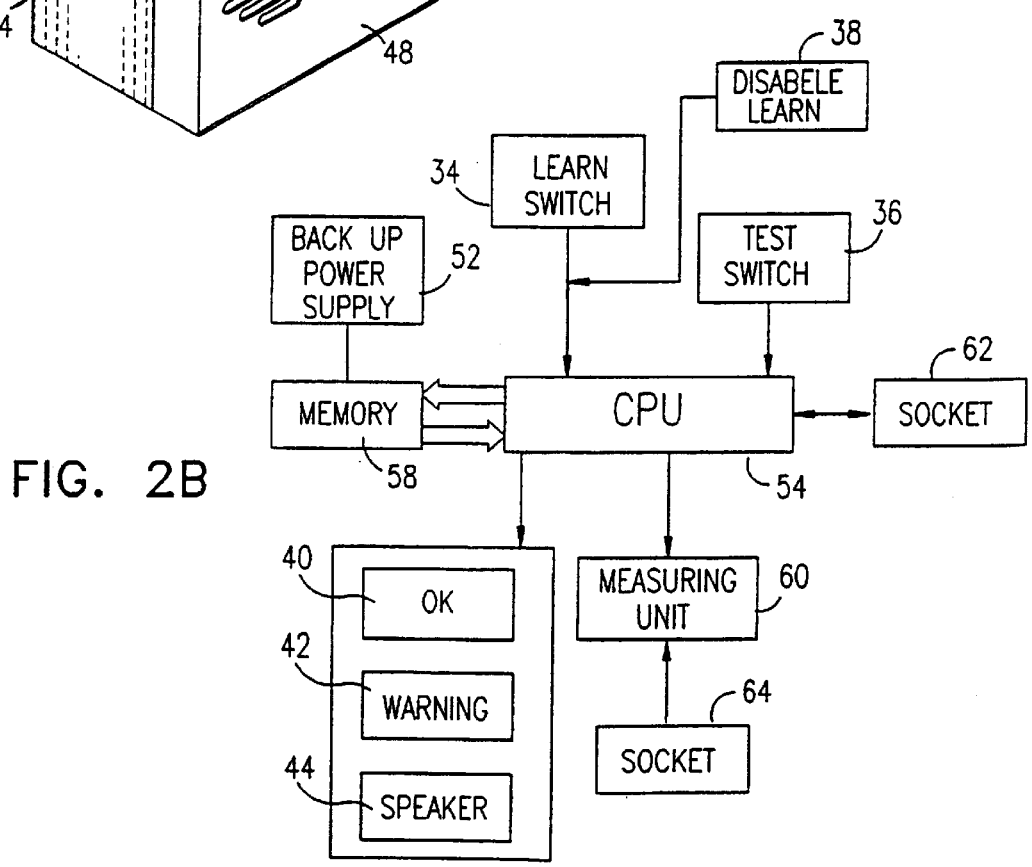
FIG. 2B is a schematic block diagram of the components of the verification device of FIG. 2A, in accordance with a preferred embodiment of the present invention.

FIGS. 2A and 2B illustrate verification device 32, in accordance with a preferred embodiment of the present invention. Verification device 32 is preferably contained in a pocket-size box. The device preferably includes a power source 50, to provide power for its operation. Power source 50 is preferably a low-voltage durable battery, although any power source may be used. Preferably, verification device 32 has a guide 46, which facilitates precise placement of verification device 32 on anchor point 30 (FIG. 1). Guide 46 preferably comprises a portion extending from the box of device 32, which is meant to be placed by a user against anchor point 30, preferably in a specific orientation. Verification device 32 includes a control panel 48, which is preferably on a side of the device, opposite guide 46. The control panel preferably includes a learn switch 34, which initiates a learn stage, and a test switch 36 which initiates a test stage, as described below. In addition, panel 48 has a speaker 44 and/or an "OK" display 40 and a warning display 42, which notify the user whether the tube is properly located and/or other control information. Alternatively, verification device 32 includes LEDs or any other suitable indicators for conveying information to the user.

The learn stage of verification device 32 is used to record information relating to the position of tube 22 within the patient's body 20. The test stage is used to confirm that tube 22 did not move substantially within the patient's body 20. Preferably, both learn and test stages are carried out by a CPU 54 located within device 32. Other elements of device 32 shown in FIG. 2B are described below with reference to methods of operating the device.

Figure 3:
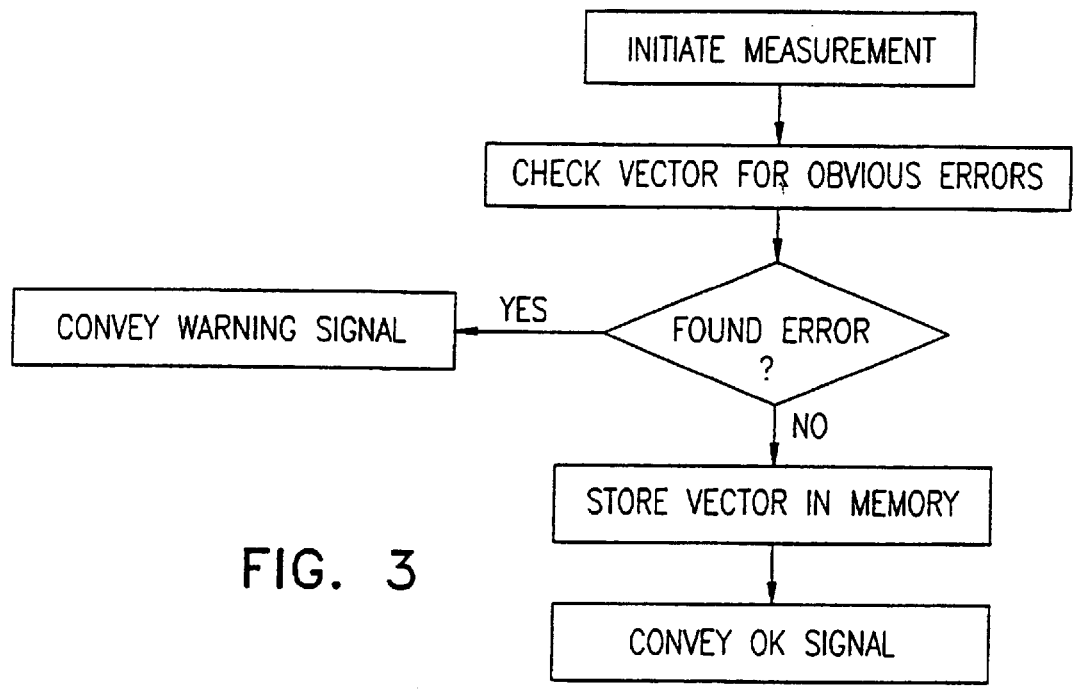
FIG. 3 is a flow chart showing the actions of the device of FIG. 2A in a learn stage, in accordance with a preferred embodiment of the present invention.

FIG. 3 is a flow chart of the operations of a learn program in CPU 54, carrying out the learn stage, in accordance with a preferred embodiment of the present invention. Preferably, the learn program initiates the operation of a measuring unit 60 which measures, as described below, one or more control parameters, forming a control vector, relating to the location of sensor 28 at tube outlet 26.

CPU 54 receives measurement results from measuring unit 60, and preferably checks them for errors. Such errors could include values beyond a predetermined acceptable range, malfunction of the measurement unit, etc. If no errors are detected, the control vector is stored in a memory 58. Memory 58 is preferably a small-capacity, non-volatile, read/write memory chip, as is known in the art. Alternatively, a back-up power supply 52 provides power to memory 58, in order to avoid loss of the parameter values stored in the memory in case of malfunction of power source 50.

If the one or more parameters are properly measured and stored, an "OK" signal is conveyed to the user, preferably by lighting up OK display 40 on panel 48. However, if the measurement was not successful, for example, if an illegal value was received or a malfunction in verification device 32 was found, a warning signal is conveyed to the user, preferably by lighting warning display 42 on the panel, and no values are stored. Alternatively or additionally, speaker 44 is used to signal the user, for example, by sounding an alarm or audio message.

Figure 4:
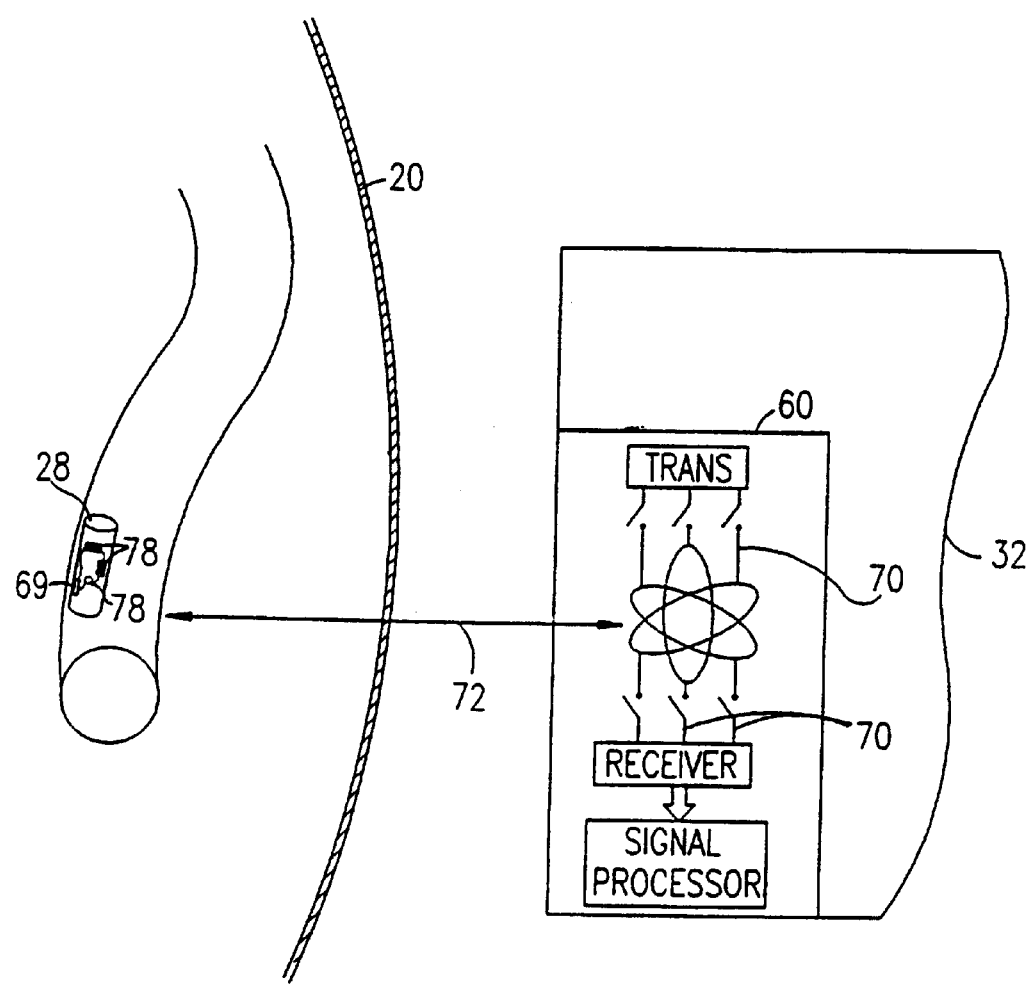
FIG. 4 is a schematic side view of a sensor and a measurement unit in accordance with a preferred embodiment of the present invention.

FIG. 4 shows details of sensor 28 and measuring unit 60, in accordance with a preferred embodiment of the present invention. Sensor 28 preferably comprises three coils 78 connected in parallel or in series and aligned in three orthogonal directions to ensure that sensor 28 will respond to a magnetic field transmitted towards it, regardless of the sensor's orientation. Coils 78 are preferably miniature coils, as described, for example, in PCT patent application PCT/GB93/01736, PCT publication WO94/04938, PCT publication WO96/05768, or PCT patent application no. PCT/IL97/00009, filed Jan. 8, 1997, which is assigned to the assignee of the present application. The disclosures of all of these PCT documents are incorporated herein by reference. In an exemplary embodiment of the present invention, sensor 28 is cylinder shaped with a cross section of 1.2 mm and length of about 8 mm. Alternatively or additionally, sensor 28 comprises one or more coils printed on a substrate using a photolithographic technique, as is known in the art, preferably as part of an assembly including two or more such coils, oriented substantially orthogonally.

In a preferred embodiment of the present invention, tube 22 is inserted into the patient's body with the guidance of a magnetic field position determining system and sensor 28. The position determining system may be, for example, as described in U.S. Pat. Nos. 5,558,091, 5,391,199 or 5,443,489, or in International Patent Publication WO94/04938 or WO96/05768, which are incorporated herein by reference. Use of such a position determining system allows precise insertion of tube 22 according to coordinates registered by the position determining system. After tube 22 is inserted, sensor 28 is used by verification device 32, in order to register and confirm the location of tube 22. Thus, sensor 28 is used both for insertion of tube 22 and for later location confirmation.

It is noted that position confirmation can also be performed by the position determining system. However, due to the simplicity, portability and low cost of verification device 32, a home user is preferably given verification device 32 rather than a position determining system.

Measuring unit 60 comprises at least one radiator coil 70, preferably three such coils. When unit 60 is operated, electric currents, preferably AC currents of different frequencies, are passed through coils 70, inducing respective magnetic fields in their proximity. Alternatively or additionally, the currents are passed through coils 70 consecutively, with a suitable delay from one coil to the next. Respective currents are induced in coils 78 of sensor 28 due to magnetic coupling with coils 70. The amplitudes of the induced currents are generally inversely proportional to the cube of the distance between the measuring unit and the sensor. The induced currents in coils 78 induce counter-currents in coils 70, which are also a function of the distance between unit 60 and sensor 28. The amplitudes of the counter-currents in coils 70 are measured, and their values preferably form the vector, which is a function of the distance 72 between measuring unit 60 and sensor 28. Preferably, the magnetic coupling allows confirmation of the position of sensor 28 over a range of at least fifteen centimeters, and with a resolution no less than half a centimeter in the location of the tube.

Preferably, sensor 28 further includes electronic circuitry 69, for example, oscillator circuitry, coupled to sensor coils 78. Circuitry 69 receives the induced currents from coils 78, and responsive to these currents, generates signals in coils 78 which are received by measuring unit 60. Circuitry 69 may comprise active circuit elements, which receive operating power from unit 60 via coils 78, in a manner similar to that used in contactless smart cards, as is known in the art. Preferably, circuitry 69 provides delay between the induction of currents in sensor 28 and the induction of counter-currents in measuring unit 60. The delay allows unit 60 to measure the counter-currents in coils 70 without the interference of the inducing currents. Alternatively, measuring unit 60 measures the amplitude difference of the current flowing in coils 70 caused by the signal induced by sensor 28.

Circuitry 69 may further include a resonant circuit, which responds to a specific frequency, such as 40 kHz. Unit 60 transmits the specific frequency and measures the resonance signal generated by circuitry 69.

Figure 5A:
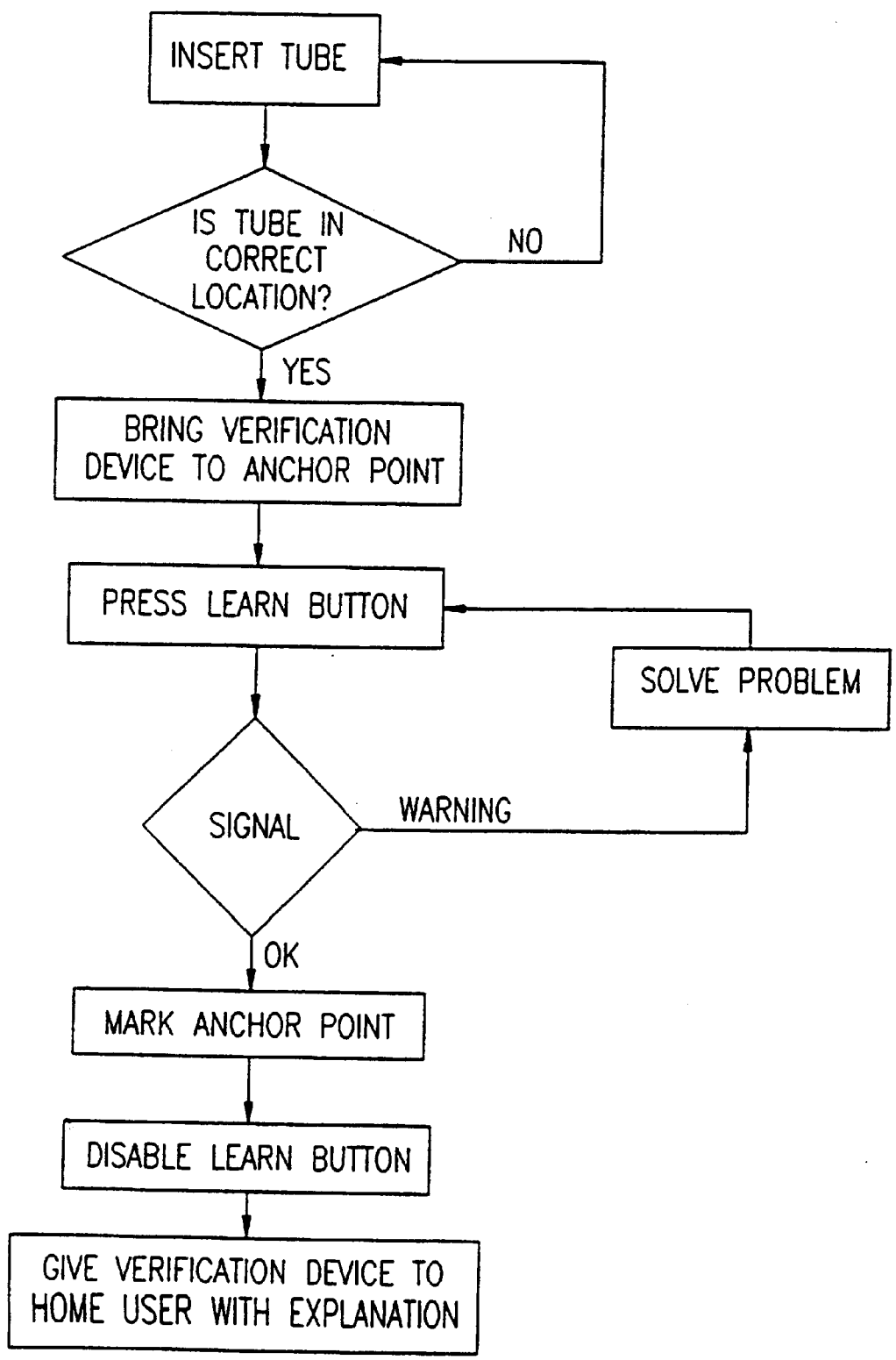
FIG. 5A is a flow chart showing the actions of a physician in a learn stage, in accordance with a preferred embodiment of the present invention.

FIG. 5A illustrates actions of a physician or another member of a clinical staff in the learn stage of operation of device 32, in accordance with a preferred embodiment of the present invention. After insertion of tube 22, the physician preferably confirms that the tube is in the patient's stomach, using any method known in the art, such as X-ray imaging or magnetic field position determination. In a further embodiment of the present invention, verification device 32 has an additional, location-finding mode of operation, in which a professional can locate outlet 26. In this mode, verification device 32 reports the parameter values from unit 60 directly to the professional user, and does not simply provide a verification signal. According to a few measurements of the parameters, made in different locations, the professional user can detect the outlet of the tube and confirm that it is in its correct location. The location-finding mode could work as described, for example, in U.S. Pat. No. 5,099,845, U.S. Pat. No. 5,425,382, or in U.S. Pat. No. 4,905,698, which are incorporated herein by reference.

If the physician determines, on the basis of imaging or of measurements in the location-finding mode, that tube 22 is not in its correct position, the physician brings the tube into its correct position, for example, by removing the tube and reinserting it into the patient.

After the correct location of outlet 26 is confirmed, the learn stage is performed, preferably by the physician. In the learn stage, verification device 32 is brought to anchor point 30 in a fixed orientation, preferably, such that guide 46 (see FIG. 2A) is situated on anchor point 30 (see FIG. 1). Learn switch 34 is then operated, and a signal is received from verification device 32. Preferably, learn switch 34 is operated while the location of the tube is visually authenticated as being correct, for example, while the patient is being X-rayed.

If a warning signal is received from device 32, the physician preferably finds the problem and corrects it, for example, by choosing a new anchor point or by replacing tube 22. Learn switch 34 is operated again until an OK signal is received. When the OK signal is received, anchor point 30 is preferably marked permanently on the patient's body, in order to simplify returning verification device 32 to anchor point 30.

Preferably, verification device 32 includes a learn disable switch 38, having two states. In a first state, switch 38 disables learn switch 34 so that the learn program of CPU 54 is not operated inadvertently by the patient. In a second state, used during the learn stage, switch 34 is allowed to operate normally. Alternatively, the verification device comprises two parts: a test part which is given to the home user and a learn part which is connected to the test part only for use by clinical staff members.

Preferably, after completion of the test stage, disable switch 38 is moved to the disable state. Verification device 32 is given to the patient or a home-care helper for routine location confirmation before each time the patient is to be fed.

Figure 5B:
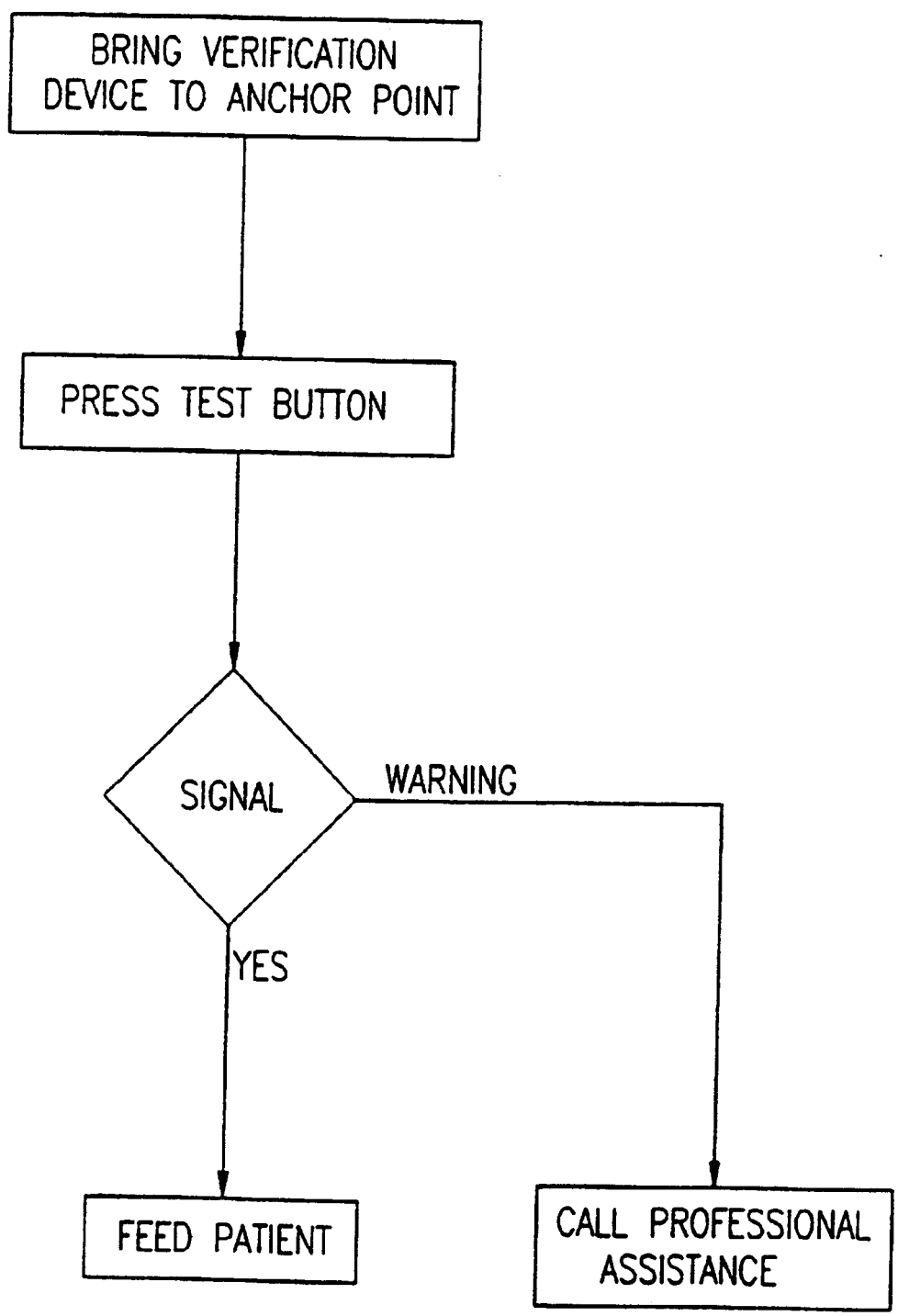
FIG. 5B is a flow chart showing the actions of a user in a test stage, in accordance with a preferred embodiment of the present invention.

FIG. 5B illustrates the actions of a home user or patient to confirm the position of the tube's outlet 26 before the patient is fed. Every time a feeding solution is to be passed through tube 22, verification device 32 is brought to anchor point 30 in the fixed orientation which was used in the learn stage. Test switch 36 is then operated, to confirm that tube 22 is properly positioned. Only if device 32 gives the "OK" signal, as described below, is the patient fed.

Figure 6:
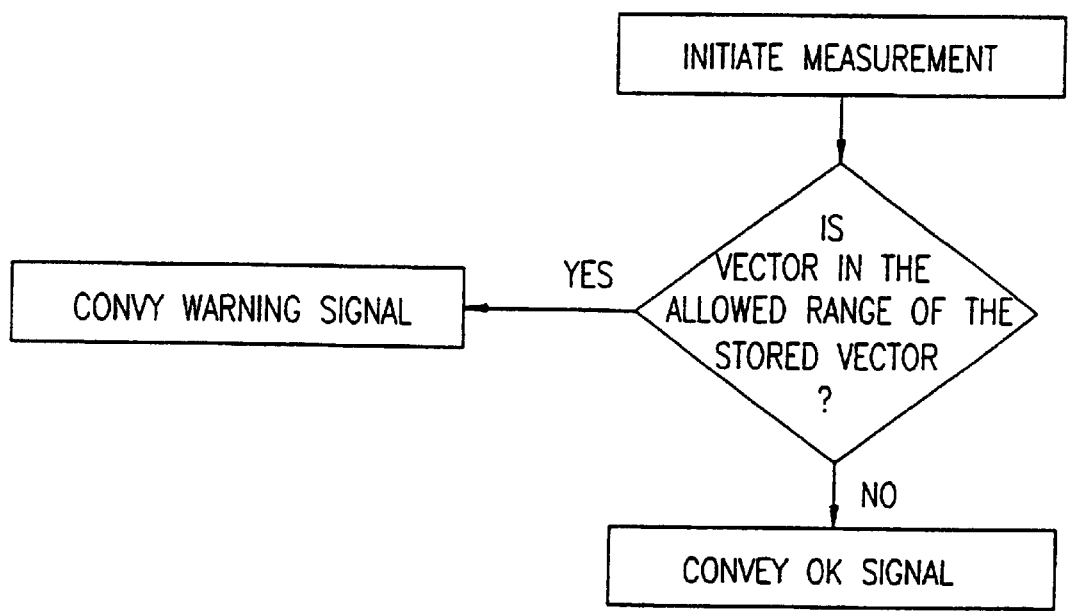
FIG. 6 is a flow chart showing the actions of the device of FIG. 2A in a test stage, in accordance with a preferred embodiment of the present invention.

FIG. 6 is a flow chart of the operations of a test program in CPU 54, carrying out the test stage, in accordance with a preferred embodiment of the present invention. Preferably, CPU 54 initiates the operation of measurement unit 60, which acquires a vector of test measurements. The test time vector from unit 60 is compared to the vector stored in memory 58 to determine whether the test vector is within an allowed range of the values stored in memory 58. If the test vector is within the predetermined range of the stored vector, an OK signal is generated and conveyed to the user. However, if one or more of the test values are not within the predetermined range of the stored vector, a warning signal is generated and conveyed to the user. The predetermined range of values is defined such that verification device 32 will generate the OK signal if outlet 26 is within a predefined distance range of its original location. Preferably, the predefined range is between 0.5 and 5 cm, most preferably between 0.5 and 2 cm, although other ranges may be defined according to specific applications of the verification device. Alternatively or additionally, the range may be adjusted by a physician or other user according to the specific application.

Accordingly, as shown in FIG. 5B, if the OK signal is received, nutritional fluid is administered to the patient through tube 22. However, if the warning signal is received, the user calls for professional assistance.

Figure 7:
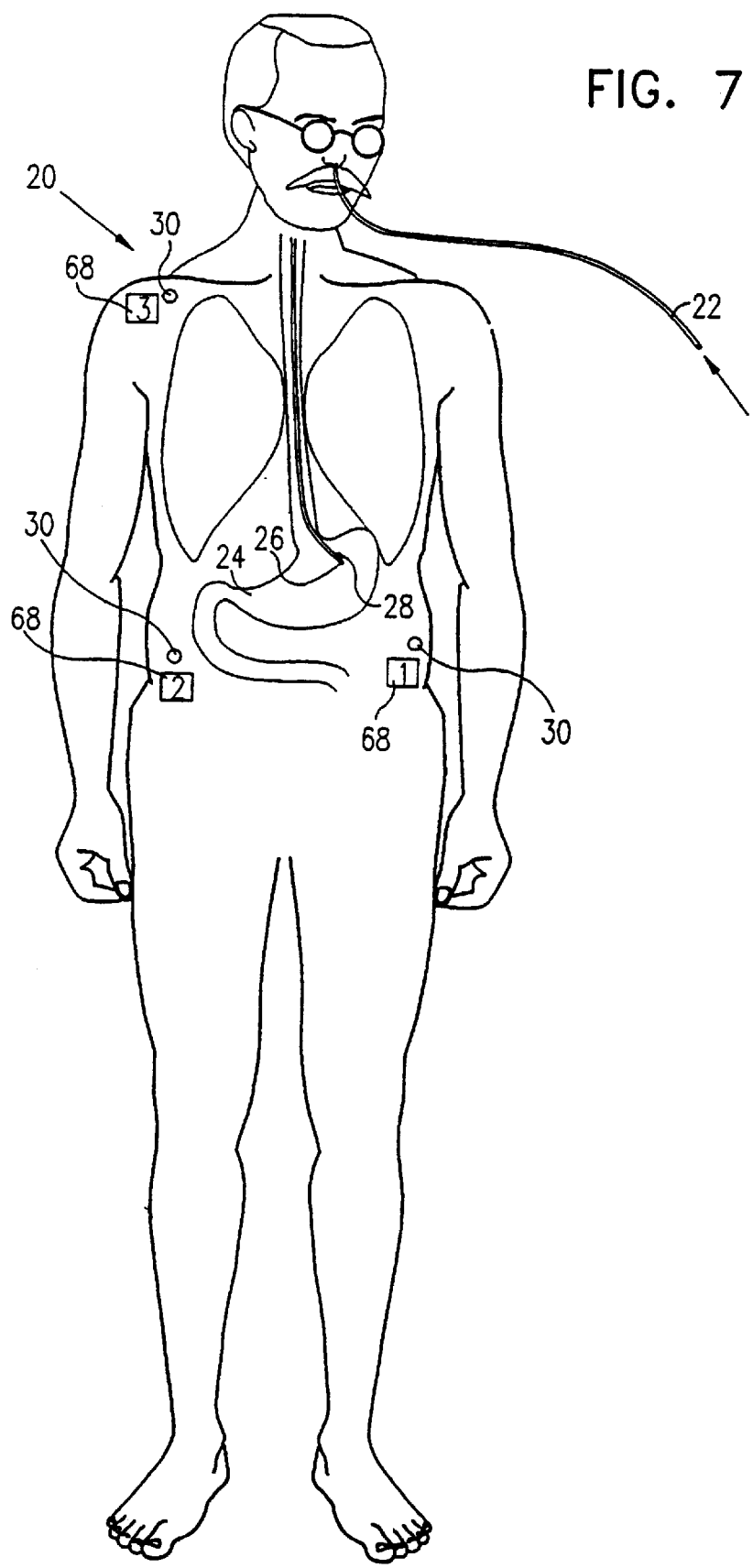
FIG. 7 is a perspective view of a patient with a feeding tube, in accordance with another preferred embodiment of the present invention.

Alternatively, as shown in FIG. 7, the one or more parameters making up the vector may be measured and compared from more than one point. This provides more accuracy to the measurement and/or allows location verification of more than one object. Also, measuring from more than one point allows better canceling out of movements of the patient.

Preferably, after the position of the tube's outlet 26 is confirmed, as described above, several points 30, preferably three points, are marked on the patient's body 20. Preferably, points 30 are marked such that their order is clearly identified. For example, a digit 68 may be marked next to each point 30 identifying the order. In the learn stage, verification device 32 is brought to points 30 in numerical order. At each of points 30, learn switch 34 is operated and verification device 32 registers the one or more parameters associated with the point. The parameters from all three points together form the vector stored in memory 58.

Every time tube 22 is to be used, the test stage is carried out. The user brings verification device 32 to points 30, in the same order as in the learn stage. At each of the three points, the user operates test switch 36, in order to register the parameters of the vector. Preferably, after test switch 36 is operated at all three points, a signal is generated reporting whether the tube is in its correct location. Preferably, verification device 32 notifies the user if test switch 36 was not operated at all three points. Alternatively or additionally, verification device 32 acknowledges the operation of test switch 36 and preferably notifies how many times the switch was operated in the current test stage.

Figure 8A:
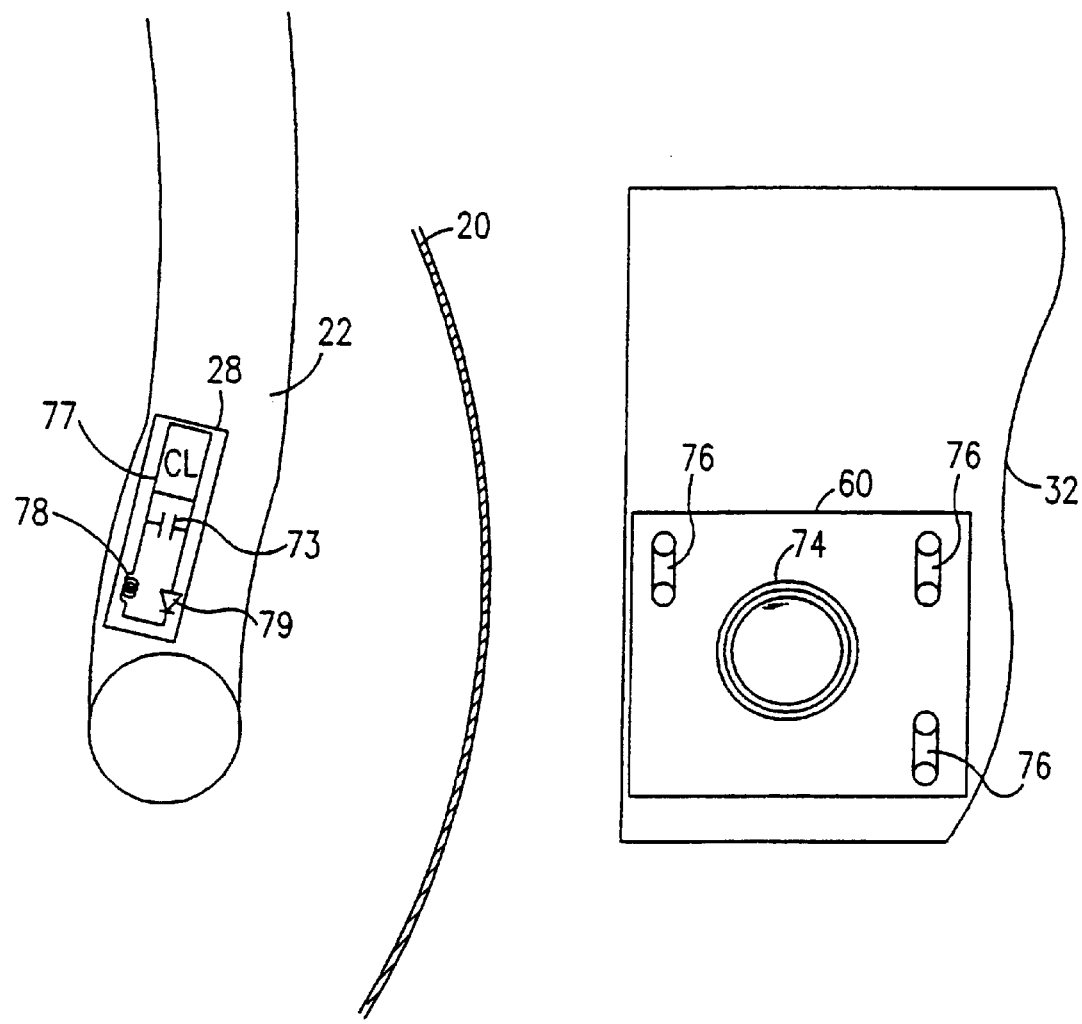
FIG. 8A is a schematic side view of a sensor and a measurement unit, in accordance with another preferred embodiment of the present invention.

FIG. 8A illustrates details of measurement unit 60 and sensor 28, in accordance with another preferred embodiment of the present invention. Unit 60 comprises an activating coil 74, for inducing currents within sensor 28, and a plurality of separate receiving elements 76. Preferably, unit 60 includes three elements 76 at different locations within device 32, each element preferably comprising three orthogonal coils 78, arranged to sense magnetic fields generated by sensor 28. Using elements 76 having three orthogonal coils ensures that fields generated by sensor 28 are received by at least one of the coils of each element 76, regardless of the relative orientation between element 76 and sensor 28. Thus, sensor 28 may include only one coil 78, occupying minimal space and having low complexity. The use of the plurality of elements 76 improves the accuracy of unit 60 and in some preferred embodiments, allows unit 60 to determine the location of tube 22 in the location-finding mode.

Sensor 28 comprises a single coil 78 and a capacitor 73, connected in series with a diode 79. Preferably, a current clamping circuit 77, as is known in the art, is connected in parallel with the capacitor. Preferably, sensor 28 comprises a flexible printed circuit and/or is produced by VLSI methods. Thus, sensor 28 may be very small and is easily mounted on or inserted in tubes and other medical tools inserted into patients.

When unit 60 is operated, a current pulse is passed through activating coil 74, so as to generate a magnetic field in the vicinity of sensor 28. The current generated in coil 78 in response to the field charges capacitor 73 through diode 79. After the termination of the current pulse, capacitor 73 discharges through clamping circuit 77 and coil 78, thus generating a magnetic field, which is detected by elements 76.

Preferably, capacitor 73 has large enough capacitance, for example, 0.1 μF, to store a substantial charge, and is charged to a voltage at least equal to a predetermined reference voltage, for example, 1.3V, when unit 60 is in sufficient proximity to sensor 28. During discharge of the capacitor, clamp circuit 77 operates as a constant current source, so that the current through coil 78 is constant for a period after deactivation of activating coil 74. During this period, unit 60 measures the currents through elements 76 and determines accordingly, at least one parameter associated with the location of sensor 28 on tube 22. Preferably, the at least one parameter is used to determine the position of the sensor, using algorithms known in the art, as described, for example, in PCT Patent Publication WO94/04938.

Figure 8B:
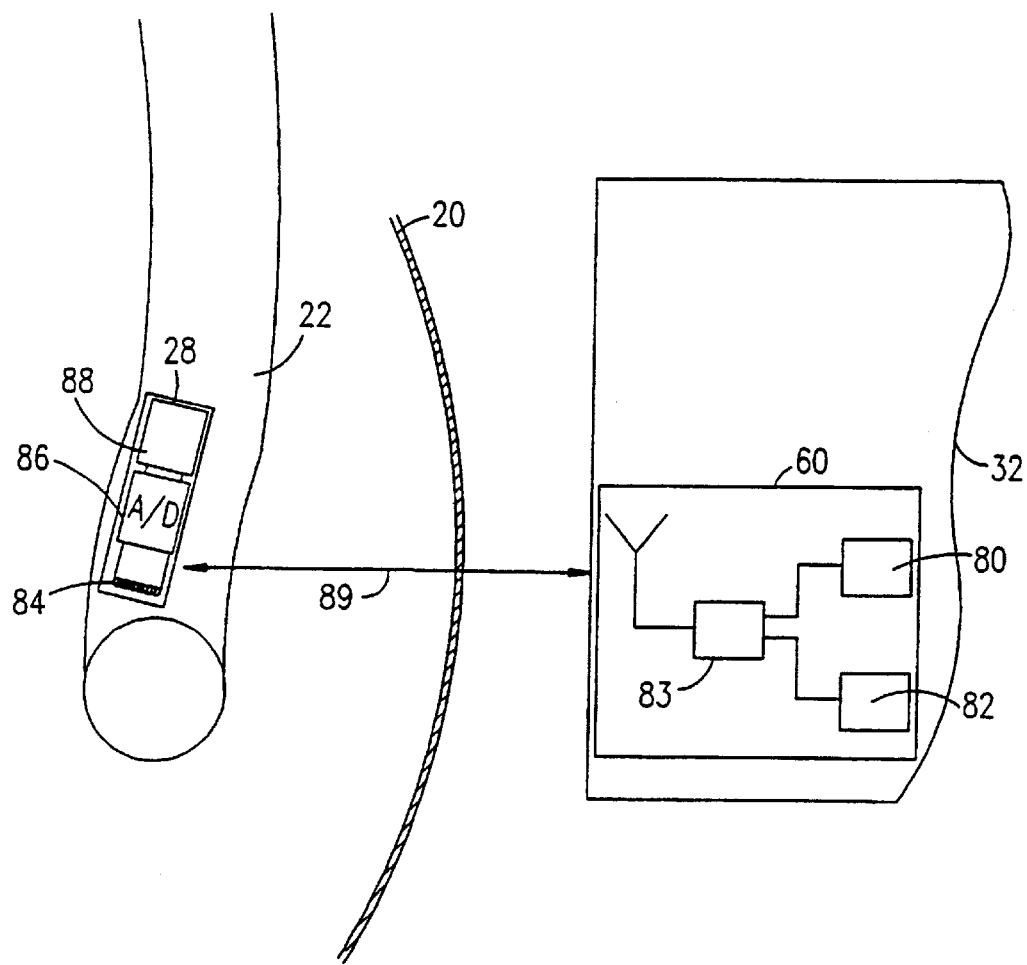
FIG. 8B is a schematic side view of a sensor and a measurement unit, in accordance with another preferred embodiment of the present invention.

FIG. 8B illustrates another alternative preferred embodiment of the present invention, in which the measurement of a parameter vector is based on the amplitude of a radio frequency (RF) signal received by sensor 28. In this embodiment, unit 60 preferably comprises an RF transmitter 80 and an RF receiver 82 and a modulator/demodulator 83 connected thereto. Alternatively, a single transducer may serve as both transmitter and receiver. Sensor 28 preferably comprises an RF transmitter/receiver 84 and an A/D circuit 86 which, converts the RF energy to digital form. Calculating circuitry 88 within sensor 28 measures the amplitude of the signal and calculates a distance 89 between sensor 28 and device 32, based thereon. Distance 89 and/or another property of the RF signal are then transmitted by transmitter/receiver 84 to device 32, preferably in the form of a digital signal, which records the distance or property in the parameter vector.

Figure 9:
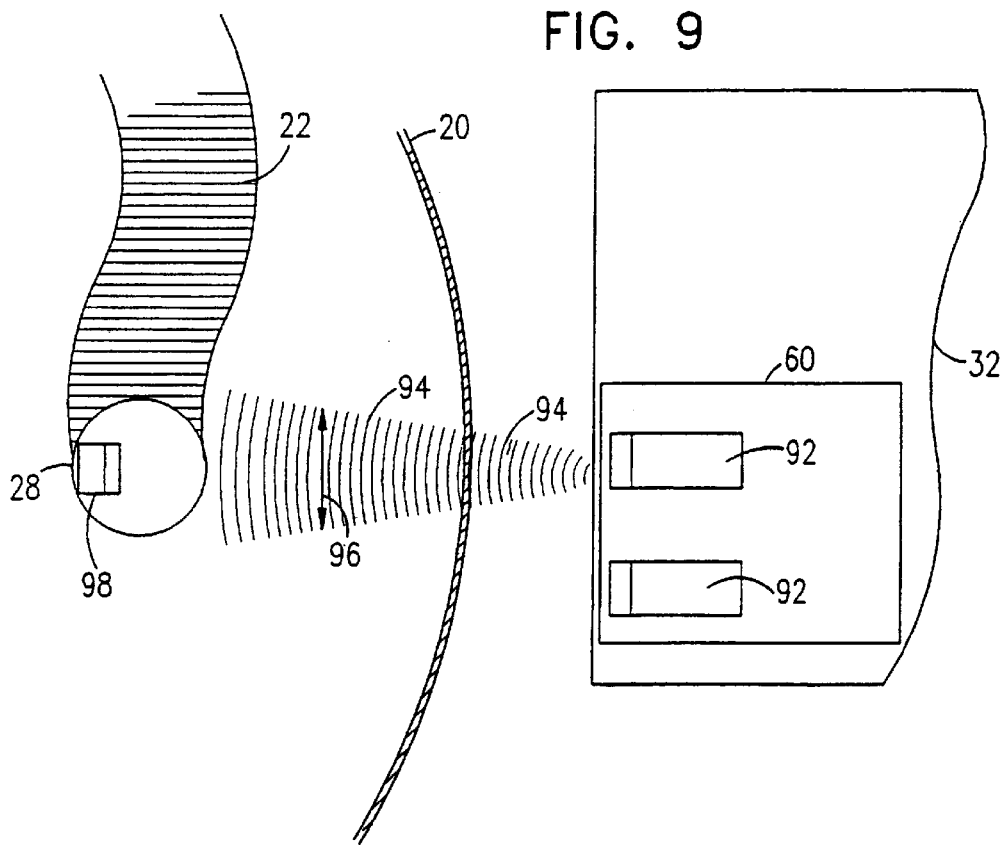
FIG. 9 is a schematic side view of a sensor and a measurement unit, in accordance with still another preferred embodiment of the present invention.

FIG. 9 shows details of measuring unit 60 and sensor 28, in accordance with another preferred embodiment of the present invention. In this embodiment, measuring unit 60 comprises one or more transducers 92 of ultrasonic waves. One of transducers 92 transmits an acoustic wave 94 when the operation of unit 60 is initiated. Sensor 28 preferably comprises a miniature passive transponder 98, as is known in the art, which reflects wave 94 back towards unit 60. One of transducers 92 receives wave 94 and registers its amplitude and/or propagation time for use as a parameter indicative of the location of outlet 26. Alternatively or additionally, a noise level or variance of wave 94 are used as parameters.

If wave 94 is not incident on transponder 98, it will not be reflected back toward transducers 92 and a signal to this effect will be generated by unit 60. It is noted, however, that wave 94 spreads as it propagates and thus covers an area 96. Therefore, slight lateral movements of the sensor or of device 32 will not substantially affect the measurement by unit 60. Thus, unit 60 provides an approximate measure of the sensor's location, with sufficient accuracy to warn of substantial changes in the location of tube 22. Due to the spread of wave 94, the wave's amplitude decreases as a function of distance during propagation. Therefore, the amplitude of the received wave is dependent on the distance between outlet 26 and verification device 32, and is appropriate for use as a parameter in the control vector.

Figure 10:
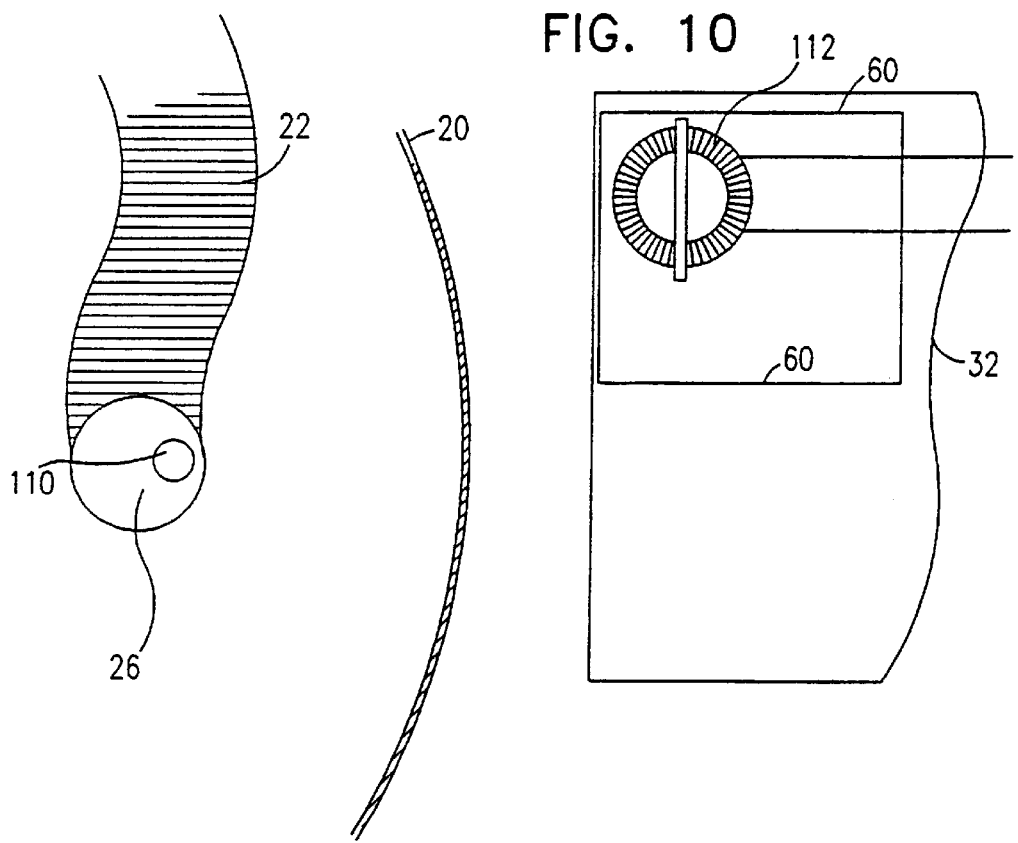
FIG. 10 is a schematic side view of a sensor and a measurement unit, in accordance with yet another preferred embodiment of the present invention.

FIG. 10 illustrates details of sensor 28 and measuring unit 60, in accordance with another preferred embodiment of the present invention. In this embodiment, sensor 28 comprises a magnet 110, which generates a static magnetic field. Measuring unit 60 comprises a magnetometer 112, which measures the amplitude of the magnetic field in its proximity. The amplitude of the magnetic field at meter 112, is dependent on the distance between magnet 110 and meter 112. Preferably, magnetometer 112 comprises one or more flux-gate toroidal sensors, as described, for example, in U.S. Pat. No. 5,425,382.

Figure 11:
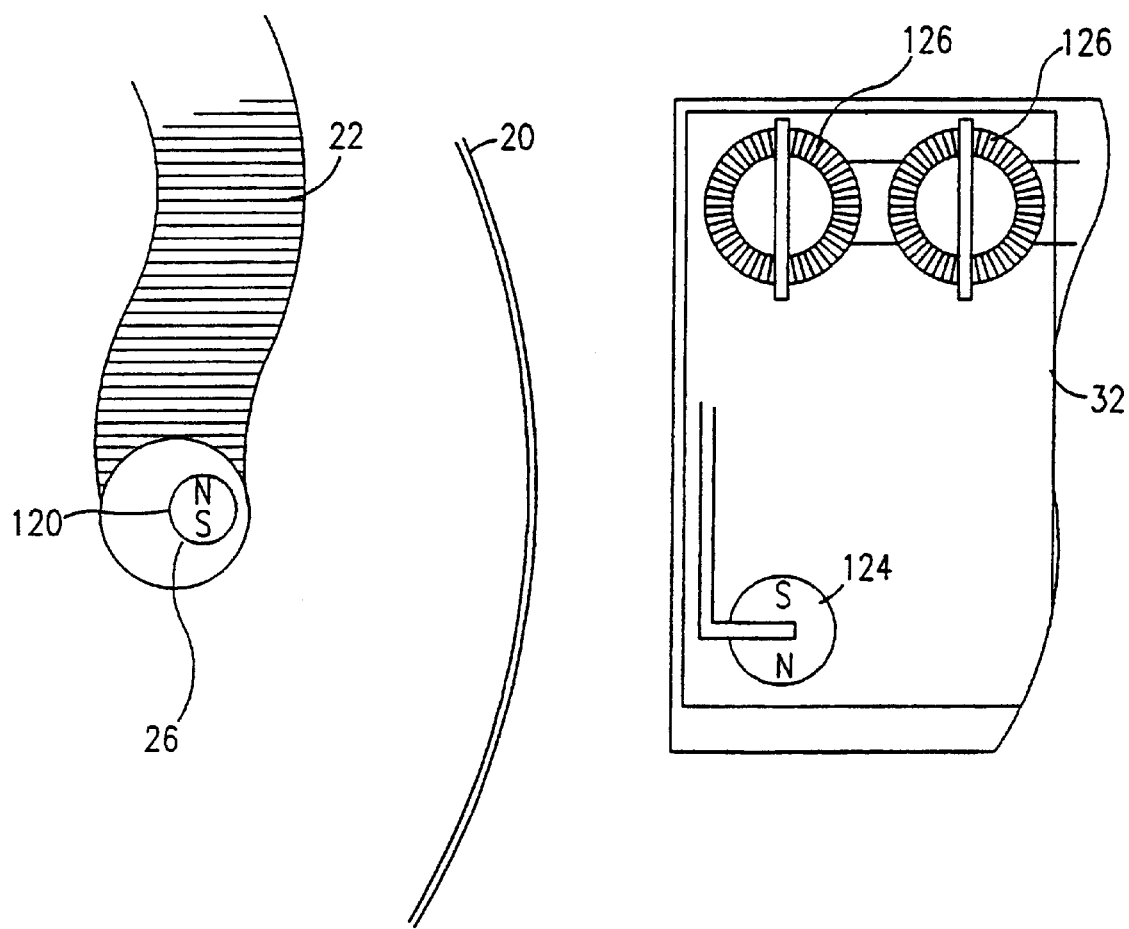
FIG. 11 is a schematic side view of a sensor and a measurement unit, in accordance with an alternative preferred embodiment of the present invention.

FIG. 11 illustrates details of measurement unit 60 in accordance with a further preferred embodiment of the present invention. Sensor 28 comprises a rotatable magnet 120, which rotates in response to an external rotating magnet 124 located outside of the patient, preferably within verification device 32. When measurement unit 60 is operated, external magnet 124 is rotated, causing magnet 120 to rotate due to coupling of its magnetic field with the rotating field of magnet 124. When magnet 120 rotates, it creates a magnetic AC field, which is sensed by measuring unit 60. Preferably, measuring unit 60 includes at least two magnetometer detectors 126, which determine one or more parameters of the magnetic field. Preferably, unit 60 distinguishes between the field of magnet 120 and that of magnet 124 by detecting the change in the overall magnetic field between the magnetometers. Alternatively, the magnetic field of magnet 120 is measured only after magnet 124 stops rotating. In a preferred embodiment of the present invention, the magnetometer detectors determine the angular position of the magnet, relative to verification device 32. Magnetometer detectors 126 are preferably as described in U.S. Pat. No. 5,002,137, which is incorporated herein by reference, but may also be of other types known in the art. It is noted that measurements acquired using a magnetic AC field are generally more accurate than measurements acquired using DC magnetic fields.

In some preferred embodiments of the present invention, the parameter vector is formed of a plurality of different parameters, measured using different methods. Such a vector enhances the accuracy of the verification device. Every time the measurement unit is operated, all the parameters of the vector are preferably measured.

Figure 12:
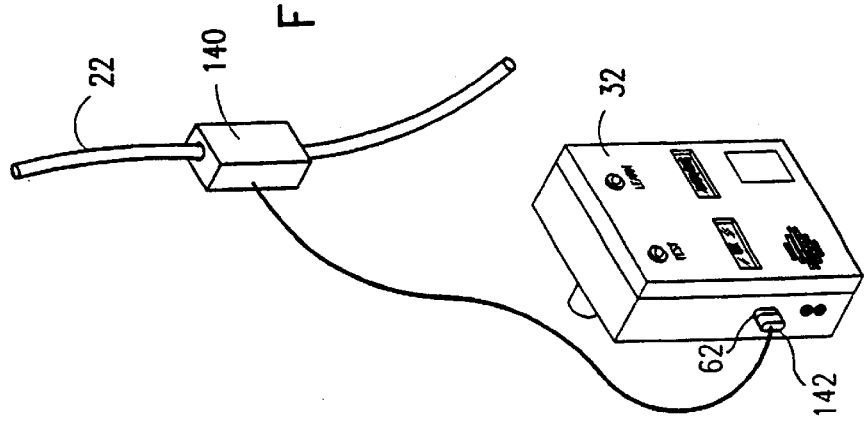
FIG. 12 is a perspective view of a fluid gating system, in accordance with a preferred embodiment of the present invention.

FIG. 12 shows a fluid control valve 140, in accordance with a preferred embodiment of the present invention. Preferably, verification device 32 includes a socket 62, through which device 32 passes the verification signals it generates, preferably in addition to displaying them to the user, as described above. Valve 140 is preferably situated on tube 22 and is operationally connected to the verification device, preferably through control wires connected to a plug 142 inserted into socket 62. Valve 140 prevents flow through tube 22, unless an OK signal is generated by verification device 32, in which case valve 140 allows flow through tube 22 for a predetermined period, of a length sufficient for feeding the patient. Thus, feeding solution will not be allowed to pass through tube 22 if there is a suspicion that tube outlet 26 is not properly positioned in the patient's stomach, or if the position of tube 22 was not confirmed prior to attempting insertion of the feeding solution.

Figure 13:
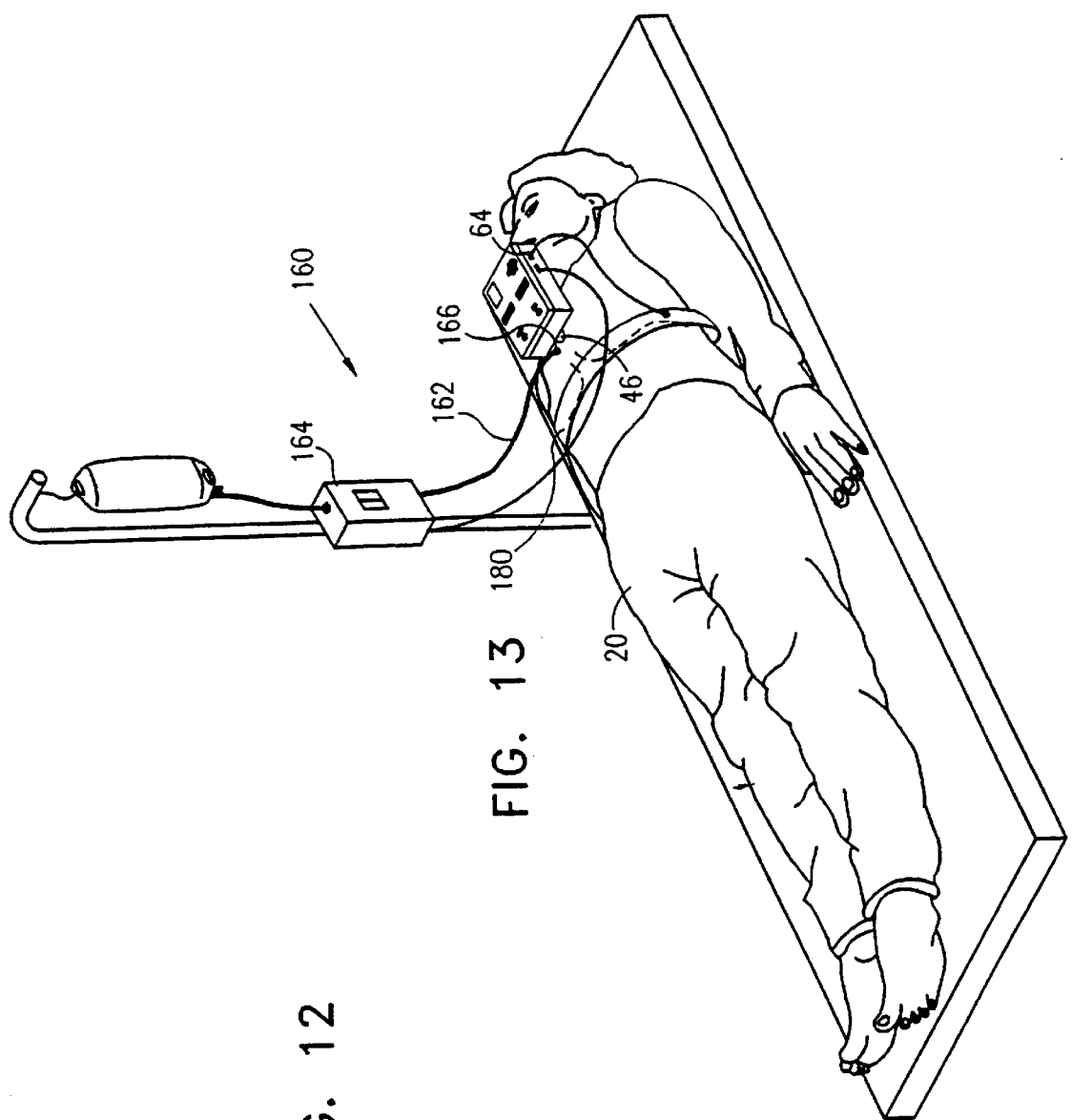
FIG. 13 is a perspective view illustrating the use of the device of FIG. 2A in controlling fluid flow, in accordance with another preferred embodiment of the present invention.

FIG. 13 shows patient 20 with an automatic infusion system 160, in accordance with another preferred embodiment of the present invention. An infusion tube 162 runs through an infuision pump 164 into patient 20. The outlet 166 of infusion tube 162 is preferably positioned in the superior vena-cava of patient 20.

Verification device 32 is fixed at anchor point 30 on patient 20, at a substantially constant distance from the superior vena cava, regardless of the patient's rest position. Preferably, verification device 32 is fixed to the center of the chest of patient 20, over the vena cava. Alternatively, device 32 may be fixed at another point, for example, near the patient's shoulder.

After a physician confirms that tube 162 is in the superior vena cava, the physician activates the learn switch to operate the learn stage, as described above. Preferably, after an OK signal is received, the physician disables learn switch 34 using disabling switch 38. Alternatively, learn switch 34 is automatically disabled responsive to the OK signal.

Infusion pump 164 monitors the amount of medicine entering the vena cava of patient 20, as is known in the art. In accordance with a preferred embodiment of the present invention, verification device 32 is in communication with infusion pump 164, so that while the infusion is operating, infusion pump 164 periodically passes a polling signal to verification device 32 requesting the operation of the test program. Verification device 32 makes a test measurement of the parameter vector and generates a response signal, which is returned to infusion pump 164. If an OK signal is received by infusion pump 164, the infusion is allowed to flow into the patient. However, if a warning signal is received, operation of pump 164 is interrupted, and a nurse is called, for example, by sounding an alarm either by infusion pump 164 or by verification device 32.

Alternatively, verification device 32 may operate automatically, continuously or intermittently, independent of infusion pump 164. As long as verification device 32 generates OK signals, infusion pump 164 is allowed to operate independently. However, if a warning signal is generated, the operation of pump 164 is disabled and a nurse is called.

In a preferred embodiment of the present invention a respiratory belt 180 gates the operation of device 32. Accordingly, when infusion pump 164 requests the operation of device 32, the operation of device 32 is delayed until the patient is in a predetermined portion of the respiratory cycle. Signals from respiratory belt 180 are preferably passed to the verification device through socket 64, so as to disable unit 60 during a portion of the respiratory cycle, allowing measurement of the one or more parameters only during a predetermined, desired portion of the respiratory cycle, so that the effect of respiration on the measurement is substantially neutralized.

Alternatively or additionally, the breathing of the patient is compensated for by having unit 60 repeatedly measure the one or more parameters over a period of multiple breaths, preferably in both the learn mode and, later, the test mode. CPU 54 stores in memory 58 the maximum and minimum values of the one or more parameters during the period.

Afterwards, the test program of CPU 54 compares the maximum and minimum values received by unit 60 in the test mode, to the stored values. If the maximum and minimum values at the later time are within a predetermined range of the stored maximum and minimum values, the OK signal is generated. Thus, the effects of the patient's breathing are taken into account without reducing the accuracy of verification by device 32.

Figure 14:
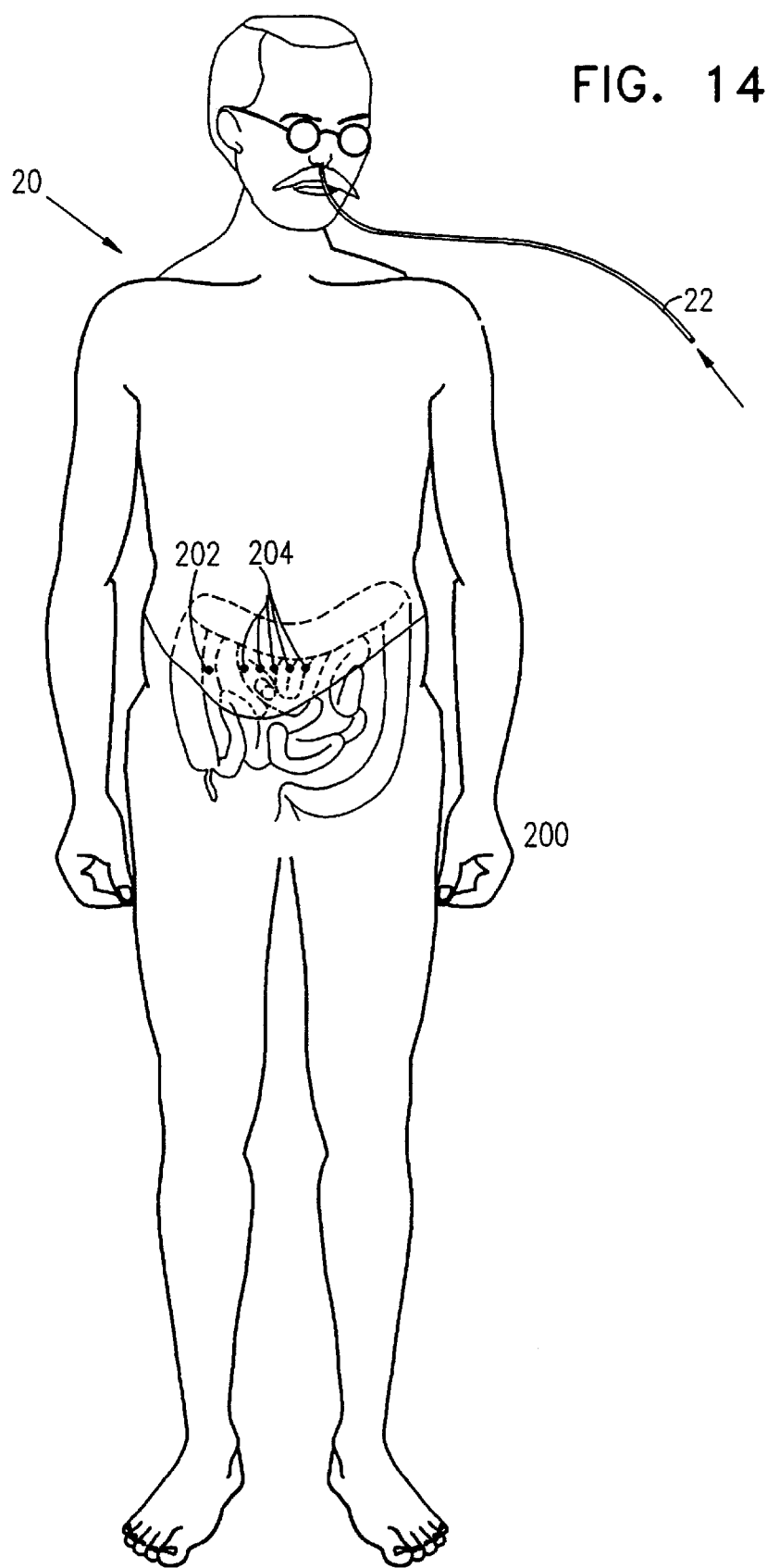
FIG. 14 illustrates the use of the verification device of FIG. 2A to follow up on the position of an object within a patient, in accordance with a preferred embodiment of the present invention.

FIG. 14 illustrates the use of verification device 32 to follow up on or track the position of an object, such as a Murphy button 200, within patient 20, in accordance with another preferred embodiment of the present invention. In order to track the location of Murphy button 200, the patient is given a verification device 32. First, device 32 is brought to a point 202 marked on the patient's skin above the location of the Murphy button 200 and is operated in the learn mode.

At later times, according to instructions from the physician, the patient brings verification device 32 to the area of the Murphy button and operates the test switch. If a warning signal is received, verification device 32 is moved slightly and the test switch is operated again. This procedure continues until an OK signal is received. Preferably, a point 204 at which verification device 32 is located when the OK signal is received is marked on the skin, preferably along with the date and time the OK signal was received. This procedure is repeated intermittently, and thus a map is formed of the progress of the Murphy button. A physician can thus follow up on the movement of the Murphy button without having to repeatedly examine and/or X-ray the patient to register the position of the button.

It will be appreciated that the preferred embodiments described above are cited by way of example, and the full scope of the present invention is limited only by the claims.

What is claimed is:

1. A system for determining a position of an object inserted into a patient's body, said system comprising:

an object having a sensor, said object being inserted into said patient's body wherein said sensor is adapted to be located within said patient's body, said sensor providing a first sensor signal and a second sensor signal; and a verification device for use outside of said patient's body, said verification device having a measuring unit for receiving said first sensor signal and said second sensor signal provided by said object, said verification device also having a memory device, said verification device being operable in a learn mode and a test mode, wherein in said learn mode, said first sensor signal is provided by said object and received by said measuring unit, said measuring unit forming a control vector based on said first sensor signal, said control vector being stored in said memory device, and wherein in said test mode, said second sensor signal is provided by said object and received by said measuring unit, said measuring unit forming a test vector, said test vector being compared to said control vector in order to verify said position of said object within said patient, wherein said verification device includes a CPU for comparing said test vector to said control vector, said CPU having a predetermined value range, said CPU comparing said control vector to said predetermined value range, said control vector being stored in said memory device when said control vector is within said predetermined value range, wherein said measuring unit generates a first measuring signal and a second measuring signal, said first measuring signal and said second measuring signal being provided to said sensor of said object, said first measuring signal inducing said first sensor signal and said second measuring signal inducing said second sensor signal, said verification device including a power source, and wherein said verification device is positioned at an exterior surface of said patient's body.

2. The system according to claim 1, wherein said verification device is operated in said test mode when said verification device is aligned with said at least one anchor point.

3. The system according to claim 2, wherein said verification device includes a guide for alignment with said at least one anchor point.

4. The system according to claim 3, wherein said verification device includes at least one visual display.

5. The system according to claim 4, wherein said verification device includes at least one audio display.

6. The system according to claim 5, wherein said verification device has a display for indicating a successful measurement and a warning display.

7. The system according to claim 6, wherein said verification device has a learn switch for activating said learn mode and a test switch for activating said test mode.

8. The system according to claim 7, wherein said verification device includes a disablement switch for disabling said learn mode.

9. The system according to claim 8, wherein said memory device has a back up power supply.

10. The system according to claim 1, wherein said object is a tube.

11. The system according to claim 10, wherein said tube has an outlet.

12. The system according to claim 11, wherein said sensor is located at said outlet of said tube.

13. The system according to claim 12, including a fluid control device operatively connected to said tube and operatively connected to said verification device.

14. The system according to claim 13, including a respiratory device operatively connected to said verification device.

15. The system according to claim 1, wherein said sensor includes at least one sensor coil and said measuring unit includes at least one measuring coil.

16. The system according to claim 1, wherein said measuring unit includes at least one ultrasonic transducer and said sensor includes at least one transponder.

17. The system according to claim 1, wherein said sensor includes at least one magnet and said measuring unit includes at least one magnetometer.

18. The system according claim 17, wherein said at least one magnet is rotatable and said measuring unit includes a measuring magnet.

19. A method for determining a position of an object inserted into a patient's body comprising the steps of:

inserting an object having a sensor within a patient's body wherein said sensor is adapted to be located within said patient's body;

placing a verification device outside of said patient's body against an exterior surface of said patient's body by placing at least one anchor point on said exterior surface of said patient's body for aligning said verification device;

initiating a learning mode with said verification device by taking a first measurement of a position of said object with respect to said verification device by forming a control vector;

initiating a test mode with said verification device by taking a second measurement of said position of said object with respect to said verification device by forming a test vector; and comparing said test vector to said control vector in order to verify said position of said object.

20. The method according to claim 19, including storing said control vector in said verification device.

21. The method according to claim 20, providing a predetermined parameter range in said verification device and comparing said control vector to said predetermined parameter range.

22. The method according to claim 21, including providing a warning signal when said control vector is not within said predetermined parameter range.

23. The method according to claim 22, including comparing said test vector to said predetermined parameter range.

24. The method according to claim 23, including providing a warning signal when said test vector is not within said predetermined parameter range.

25. The method according to claim 21, including storing said control vector in said verification device when said control vector is in said predetermined parameter range.

26. The method according to claim 25, including disabling said learning mode of said verification device after said control vector is stored in said verification device.

27. The method according to claim 26, wherein said object is a tube having an outlet and said sensor is located at said outlet.

28. The method according to claim 27, including providing a fluid to said patient through said tube.

29. At The method according to claim 28, including controlling a delivery of said fluid to said patient through a fluid control device.

30. The method according to claim 29, including operatively controlling said fluid delivery through said fluid control device with said verification device.

31. The method according to claim 30, including providing a respiratory device for taking said first measurement and said second measurement with said verification device.

32. The method according to claim 28, including feeding said patient through said tube.

33. The method according to claim 19, including inducing a first signal from said sensor and inducing a second signal from said sensor with said verification device for taking said first measurement and said second measurement respectively.

34. The method according to claim 19, including taking said first measurement and said second measurement ultrasonically.

35. The method according to claim 19, including taking said first measurement and said second measurement magnetically.

36. A system for determining a position of a tube inserted into a patient's body, said system comprising:

a tube having an outlet and a sensor located at said outlet, said tube being inserted into said patient's body wherein said sensor is adapted to be located within said patient's body, said sensor providing a first sensor signal and a second sensor signal;

a verification device for use outside of said patent's body; said verification device having a measuring unit for receiving said first sensor signal and said second sensor signal provided by said tube, said verification device also having a memory device, said verification device being operable in a learn mode and a test mode, wherein in said learn mode, said first sensor signal is provided by said tube and received by said measuring unit, said measuring unit forming a control vector based on said first sensor signal, said control vector being stored in said memory device, and wherein in said test mode, said second sensor signal is provided by said tube and received by said measuring unit, said measuring unit forming a test vector, said test vector being compared to said control vector in order to verify said position of said tube within said patient;

a fluid control device operatively connected to said tube and operatively connected to said verification device; and a respiratory device operatively connected to said verification device.

37. A system for determining a position of an object inserted into a patient's body, said system comprising:

an object having a sensor, said object being inserted into said patient's body wherein said sensor is adapted to be located within said patient's body, said sensor providing a first sensor signal and a second sensor signal; and a verification device for use outside of said patent's body, said verification device having a measuring unit for receiving said first sensor signal and said second sensor signal provided by said object, said verification device also having a memory device, said verification device being operable in a learn mode and a test mode, wherein in said learn mode, said first sensor signal is provided by said object and received by said measuring unit, said measuring unit forming a control vector based on said first sensor signal, said control vector being stored in said memory device, and wherein in said test mode, said second sensor signal is provided by said object and received by said measuring unit, said measuring unit forming a test vector, said test vector being compared to said control vector in order to verify said position of said object within said patient, wherein said sensor includes at least one sensor coil and said measuring unit includes at least one measuring coil.

38. A method for determining a position of an object inserted into a patient's body comprising the steps of:

inserting an object having a sensor including at least one sensor coil within a patient's body wherein said sensor is adapted to be located within said patient's body;

placing a verification device having a measuring unit including at least one measuring coil outside of said patient's body against an exterior surface of said patient's body;

initiating a learning mode with said verification device by taking a first measurement of a position of said object with respect to said verification device by forming a control vector;

initiating a test mode with said verification device by taking a second measurement of said position of said object with respect to said verification device by forming a test vector; and comparing said test vector to said control vector in order to verify said position of said object.

* * * * *